United States Patent [19]

Bansal et al.

[11] Patent Number: 5,438,150

[45] Date of Patent: Aug. 1, 1995

[54] PROCESS FOR MAKING 1-BENZOCYCLOALKYL-1,3-DIHYDROIMIDAZOLE-2-THIONE DERIVATIVES

[75] Inventors: Rekha P. Bansal, Santa Clara; Owen W. Gooding, Los Gatos; Alexander V. Muehldorf; Counde O-Yang, both of Sunnyvale, all of Calif.

[73] Assignee: Syntex (U.S.A.) Inc., Palo Alto, Calif.

[21] Appl. No.: 233,655

[22] Filed: Apr. 26, 1994

[51] Int. Cl.$^6$ .................. C07D 233/84; C07C 231/08
[52] U.S. Cl. ........................... 548/324.5; 548/316.4
[58] Field of Search .................... 548/316.4, 324.5; 564/58, 123

[56] References Cited

U.S. PATENT DOCUMENTS 5,051,409 9/1991 Zipplies et al. .................. 514/63
5,338,862 8/1994 Aiman et al. .................. 548/316.4

OTHER PUBLICATIONS

March, J. Advanced Organic Chemistry: Reactions, Mechanisms, and Structure, Fourth Edition, 1992, McGraw-Hill, New York, p. 425.

Duncia, J. V.; Chiu, A. T.; Carini, D. J.; Gregory, G. B.; Johnson, A. L.; Price, W. A.; Wells, G. J.; Wong, P. C.; Calabrese, J. C.; Timmermans, P. B. M. W. M. The Discovery of Potent Nonpeptide Angiotensin II Receptor Antagonists: a New Class of Potent Antihypertensives. J. Med. Chem. 1990, 33, 1312.

Norlander, E. J.; Payne, M. J.; Njoroge, F. G.; Vishwanath, V. M.; Han, G. R., Laikos, G. D., Balk, M. A. A Short Enantiospecific Synthesis of 2-Amino-6,-7-dihydroxy-1,2,3,4-tetrahydronaphthalene (ADTN). J. Org. Chem. 1985, 50, 3619.

Primary Examiner—Jacqueline Haley
Attorney, Agent, or Firm—Wayne W. Montgomery

[57] ABSTRACT

The present invention relates to a process for preparing a 5-(N-substituted)aminomethyl-1-benzocycloalkyl-1,3-dihydroimidazole-2-thione (wherein the N-substituent is selected from formyl, aminocarbonyl, ($C_{1-4}$)alkylcarbonyl or trifluoro ($C_{1-4}$)alkylcarbonyl), which process comprises reacting a benzocycloalkylamine with thiocyanic acid and dihydroxyacetone to give a corresponding 5-hydroxymethyl-1-benzocycloalkyl-1,3-dihydroimidazole-2-thione and then reacting the 5-hydroxymethyl-1-benzocycloalkyl-1,3-dihydroimidazole-2-thione with a compound of the formula $H_2NC(O)R^2$ in which $R^2$ is hydrogen, amino, ($C_{1-4}$)alkyl or trifluoro($C_{1-4}$)alkyl or with an ammonium salt of the formula $NH_4^+$ $^-OC(O)R^3$ in which $R^3$ is hydrogen, ($C_{1-4}$)alkyl or trifluoro($C_{1-4}$)alkyl.

The present invention also relates to a process for preparing 5-aminomethyl-1-benzocycloalkyl-1,3-dihydroimidazole-2-thiones, which process comprises preparing a 5-(N-substituted)aminomethyl-1-benzocycloalkyl-1,3-dihydroimidazole-2-thione (wherein the N-substituent is selected from formyl, ($C_{1-4}$)alkylcarbonyl or trifluoro($C_{1-4}$)alkylcarbonyl) by the process described above and then hydrolyzing with acid.

19 Claims, No Drawings

PROCESS FOR MAKING 1-BENZOCYCLOALKYL-1,3-DIHYDROIMIDAZOLE-2-THIONE DERIVATIVES

BACKGROUND OF THE INVENTION

CROSS-REFERENCE TO RELATED APPLICATIONS

This application is related to the following co-pending application Ser. No. 08/233,835, entitled "Benzocycloalkylazolethione Derivatives", filed contemporaneously herewith and incorporated herein by reference.

1. Field of the Invention

This invention relates to a novel process for preparing 1-benzocycloalkyl-1,3-dihydroimidazole-2-thiones and the pharmaceutically acceptable acid addition salts thereof, which are dopamine β-hydroxylase inhibitors.

2. Description of the Field

Dopamine is a catecholamine neurotransmitter found predominately, along with specific dopaminergic receptors, in the central nervous system. Norepinephrine is a circulating catecholamine, which acts at discrete adrenergic receptors in peripheral systems. Dopamine β-hydroxylase (DBH) catalyzes the conversion of dopamine to norepinephrine and is found in both central and peripheral sympathetic neurons. Inhibition of DBH concurrently elevates dopamine levels by blocking its metabolism and reduces norepinephrine levels by blocking its synthesis. Thus, drugs which inhibit DBH are useful for treating diseases associated with reduced dopamine levels (e.g., Parkinson's disease) and for treating diseases associated with elevated norepinephrine levels (e.g., hypertension, congestive heart failure, etc.). Fusaric acid, a DBH inhibitor, decreases the tremors and other abnormalities associated with Parkinson's disease. Fusaric acid also reduces blood pressure in hypertensive patients; however, release of norepinephrine from the adrenal gland and a resultant tachycardia is also observed. Other more selective DBH inhibitors are known but often possess disadvantageous effects.

Certain 5-aminomethyl-1-benzocycloalkyl-1,3-dihydroimidazole-2-thiones are described as dopamine β-hydroxylase inhibitors in the above-identified co-pending application.

SUMMARY OF THE INVENTION

The present invention relates to a process for the preparation of an acid addition salt of a compound of Formula 1:

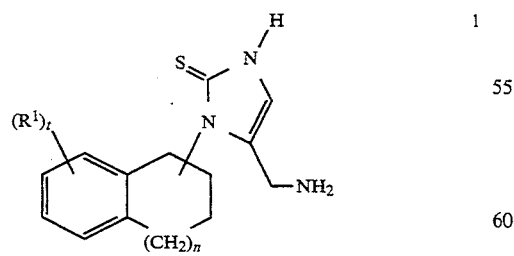

in which
n is 0, 1 or 2;
t is 0, 1, 2 or 3;
$R^1$ is independently halo, hydroxy or $(C_{1-4})$alkyloxy;
and the free base, individual isomers, and mixtures of isomers thereof; which process comprises:

(A) reacting, in the presence of acid, a compound of Formula 4:

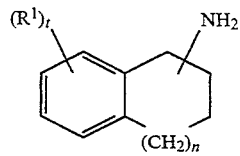

in which n, t and $R^1$ are as defined above, with thiocyanic acid and dihydroxyacetone to give a compound of Formula 3:

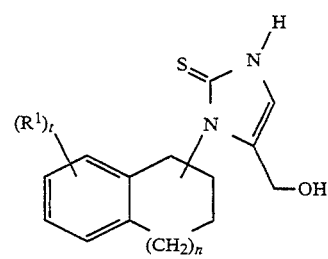

in which n, t and $R^1$ are as defined above;

(B) reacting the compound of Formula 3 with a primary compound of the formula $H_2NC(0)R^2$ or an ammonium salt of the formula $NH_4^+ -OC(0)R^2$ (in which $R^2$ is hydrogen, $(C_{1-4})$alkyl or trifluoro$(C_{1-4})$alkyl) to give a compound of Formula 2:

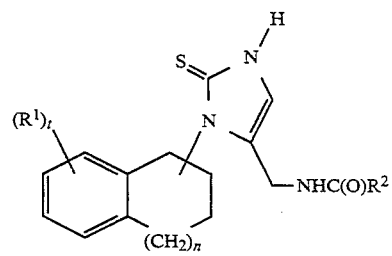

in which n, t and $R^1$ are as defined above; and (C) hydrolyzing with acid; and (D) optionally reacting the acid addition salt form of a compound of Formula 1 with an inorganic or organic base to give the corresponding free base form; and (E) optionally reacting the free base form of a compound of Formula 1 with a pharmaceutically acceptable acid to give the corresponding acid addition salt; and (F) optionally separating a mixture of stereoisomers of a compound of Formula 1 to give a single stereoisomer.

Another aspect of the present invention relates to a process for the preparation of a compound of Formula 2:

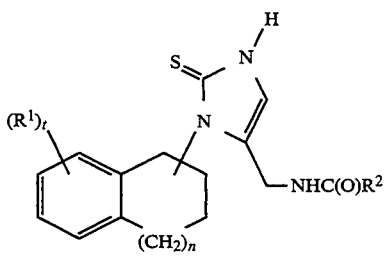

2 in which:
n is 0, 1 or 2;
t is 0, 1, 2 or 3;
$R^1$ is independently halo, hydroxy or $(C_{1-4})$alkyloxy; and
$R^2$ is hydrogen, amino, $(C_{1-4})$alkyl or trifluoro$(C_{1-4})$alkyl; and the acid addition salt, individual isomers, and mixtures of isomers thereof; which process comprises:

(A) reacting a compound of Formula 4:

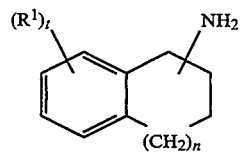

4 in which n, t and $R^1$ are as defined above, with thiocyanic acid and dihydroxyacetone to give a compound of Formula 3:

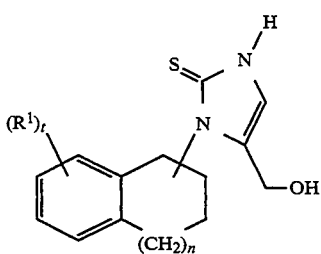

3 in which n, t and $R^1$ are as defined above; and (B) reacting the compound of Formula 3 with a primary amide of the formula $H_2NC(O)R^2$ in which $R^2$ is as defined above to give a compound of Formula 2 in which $R^2$ is as defined above or reacting the compound of Formula 3 with an ammonium salt of the formula $NH_4+ -OC(O)R^3$ in which $R^3$ is hydrogen, $(C_{1-4})$alkyl or trifluoro$(C_{1-4})$alkyl to give a compound of Formula 2 in which $R^2$ is hydrogen, $(C_{1-4})$alkyl or trifluoro$(C_{1-4})$alkyl, respectively; and (C) optionally separating a mixture of stereoisomers of a compound of Formula 2 to give a single stereoisomer.

DETAILED DESCRIPTION OF THE INVENTION

Definitions:

As used herein:

"Alkyl" means a straight or branched saturated hydrocarbon radical having from one to the number of carbon atoms designated (e.g., $(C_{1-4})$alkyl includes the radicals methyl, ethyl, prop-1-yl, prop-2-yl, but-1-yl, but-2-yl, 2-methylpropyl and 1,1-dimethylethyl).

"Trifluoroalkyl" means a radical alkyl as defined above having from one to the number of carbon atoms designated wherein is contained a trifluoromethyl group (e.g., trifluoro$(C_{1-4})$alkyl includes trifluoromethyl, 2,2,2-trifluoroethyl, 3,3,3-trifluoroprop-1-yl, 1,1,1-trifluoroprop-2-yl, etc.).

"Alkyloxy" means the radical -OR wherein R is alkyl having from one to the number of carbon atoms designated (e.g., $(C_{1-4})$alkyloxy includes the radicals methoxy, ethoxy, prop-1-yloxy, prop-2-yloxy, but-1-yloxy, but-2-yloxy, 2-methylprop-1-yloxy and 2-methylprop-2-yloxy).

"Halo" means fluoro, chloro or bromo.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Acid addition salts" means salts formed with inorganic acids such as hydrochloric acid, hydrobromic acid, sulfuric acid, nitric acid, phosphoric acid, and the like; or with organic acids such as formic acid, acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl)benzoic acid, cinnamic acid, mandelic acid, methanesulfonic acid, ethanesulfonic acid, 1,2,-ethanedisulfonic acid, 2-hydroxyethanesulfonic acid, benzenesulfonic acid p-chlorobenzenesulfonic acid, 2-naphthalenesulfonic acid, p-toluenesulfonic acid, camphorsulfonic acid, 4-methylbicyclo[2.2.-2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like.

"Pharmaceutically acceptable acid addition salts" are salts which are pharmaceutically acceptable, as defined above, and which possess the desired pharmacological activity.

The compounds of Formulae 1, 2 and 3 are 1-benzocycloalkyl-1,3-dihydroimidazole-2-thione derivatives wherein the benzocycloalkyl portion of the molecule is of the general formula:

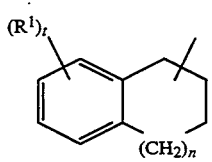

and are more specifically defined as follows:

(1) a group in which n is 0 and the monovalent carbon is at the 1- or 2-position (i.e., α- or β-position) having the formula:

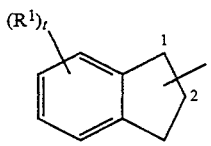

is referred to as optionally substituted indan-1-yl or indan-2-yl, respectively;

(2) a group in which n is 1 and the monovalent carbon is at the 1- or 2-position (i.e., α- or β-position) having the formula:

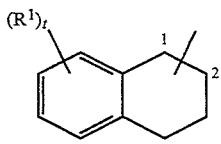

is referred to as optionally substituted 1,2,3,4-tetrahydronaphth-1-yl or 1,2,3,4-tetrahydronaphth-2-yl, respectively; and (3) a group in which n is 2 and the monovalent carbon is at the 5-, 6- or 7-position having the formula:

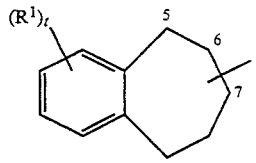

is referred to optional substituted 6,7,8,9-tetrahydro-5H-benzocyclohepten-5-yl 6,7,8,9-tetrahydro-5H-benzocyclohepten-6-yl or 6,7,8,9-tetrahydro-5H-benzocyclohepten-7-yl, respectively.

The monovalent carbon of the benzocycloalkyl group may be a chiral center. Thus, compounds of Formula 1, 2, 3 and 4 may exist as either one of a pair of enantiomers of opposite chirality or as a mixture of such enantiomers. The enantiomers are characterized by the absolute configuration of their chiral centers and described by the R- and S-sequencing rules of Cahn, Ingold and Prelog. Conventions for stereochemical nomenclature, methods for the determination of stereochemistry and the separation of stereoisomers are well-known in the art (e.g., see "Advanced Organic Chemistry", 3rd edition, March, Jerry, John Wiley & Sons, New York, 1985). Unless indicated otherwise, the illustration, description or naming of a particular chiral compound of Formula 1, 2, 3 or 4 in the specification or in the claims is intended to include both individual enantiomers and the mixtures, racemic or otherwise, thereof.

The 1,3-dihydroimidazole-2-thione portion of compounds of Formulae 1, 2 and 3 can exists in tautomeric equilibrium between its thioxo and mercapto tautomers. Compounds of Formula 1, 2 and 3 are named, illustrated or otherwise described in this application as thiones. However, it is to be understood that the mercapto tautomer is encompassed by such names, illustrations and descriptions as well.

The compounds of Formulae 1, 2, 3 and 4 are named by AUTONOM Version 1.0 by Beilstein-Institut and Springer-Verlag Berlin Heidelberg, a fully automatic computerized system for assigning IUPAC systematic nomenclature directly from the structural diagrams of organic compounds. For example, a compound of Formula 1 in which n is 1, t is 2, $R^1$ is fluoro at the 5- and 7-position and the 1,3-dihydroimidazole-2-thione group is attached at the β-position, i.e., of the formula:

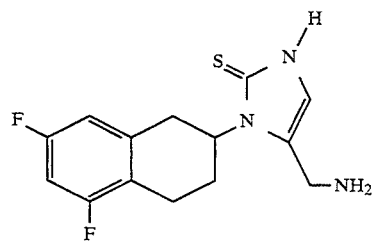

is named 5-aminomethyl-1-(5,7-difluoro-1,2,3,4-tetrahydronaphthalen-2-yl)-1,3-dihydroimidazole-2-thione.

A compound of Formula 2 in which n is 1, t is 2, $R^1$ is fluoro at the 5- and 7-position, $R^2$ is hydrogen and the 3-dihydroimidazole-2-thione group is attached at the β-position, i.e., of the formula:

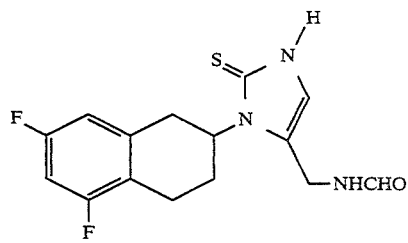

is named N-[3-(5,7-difluoro-1,2,3,4-tetrahydronaphthalen-2-yl)-2-thioxo-2,3-dihydro-1H-imidazol-4-ylmethyl]-formamide.

A compound of Formula 3 in which n is 1, t is 2, $R^1$ is fluoro at the 5- and 7-position and the 3-dihydroimidazole-2-thione group is attached at the β-position, i.e., of the formula:

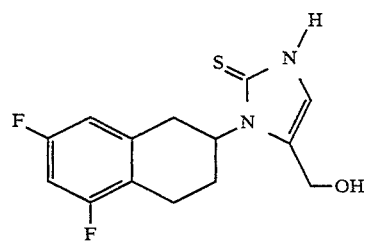

is named 5-hydroxymethyl-1-(5,7-difluoro-1,2,3,4-tetrahydro-naphthalen-2-yl)-1,3-dihydroimidazole-2-thione.

A compound of Formula 4 in which n is 1, t is 2, $R^1$ is fluoro at the 5- and 7-position and the amino group is attached at the β-position, i.e., of the formula:

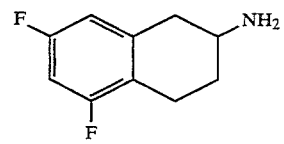

is named 5,7-difluoro-1,2,3,4-tetrahydronaphthalen-2-ylamine.

Preferred Embodiments:

While the broadest definition of this invention is set forth in the Summary of the Invention, certain processes for the preparation of compounds of Formulae 1 and 2 are preferred. For example, a preferred process for the preparation of an acid addition salt of 5-aminomethyl-1-(5,7-difluoro-1,2,3,4-tetrahydronaphthalen-2-yl)-1,3-dihydroimidazole-2-thione and the free base, individual stereoisomers, and mixtures of stereoisomers thereof; which process comprises:

(A) reacting 5,7-difluoro-1,2,3,4-tetrahydronaphthalen-2-ylamine with thiocyanic acid and dihydroxyacetone to give 5-hydroxymethyl-1-(5,7-difluoro-1,2,3,4-tetrahydronaphthalen-2-yl)-1,3-dihydroimidazole-2-thione;

(B) reacting the 5-hydroxymethyl-1-(5,7-difluoro-1,2,3,4-tetrahydro-naphthalen-2-yl)-1,3-dihydroimidazole-2-thione with a compound of the formula $H_2NC(O)R^2$ or an ammonium salt of the formula $NH_4+ \ -OC(O)R^2$ (in which $R^2$ is hydrogen, $(C_{1-4})$alkyl or trifluoro$(C_{1-4})$alkyl) to give a compound of Formula 2(a):

2(a)

in which $R^2$ is as defined above; and (C) hydrolyzing the compound of Formula 2(a) with acid; preferably wherein the 5,7-difluoro-1,2,3,4-tetrahydronaphthalen-2-ylamine is the (S)-isomer thereof, $R^2$ is hydrogen, the 5-hydroxymethyl-1-(5,7-difluoro-1,2,3,4-tetrahydronaphthalen-2-yl)-1,3-dihydroimidazole-2-thione is reacted ammonium formate and the acid is hydrochloric acid.

A preferred process for the preparation of a compound of Formula 2 comprises (A) reacting 5,7-difluoro-1,2,3,4-tetrahydronaphthalen-2-ylamine with thiocyanic acid and dihydroxyacetone to give 5-hydroxymethyl-1-(5,7-difluoro-1,2,3,4-tetrahydronaphthalen-2-yl)-1,3-dihydroimidazole-2-thione and (B) reacting the 5-hydroxymethyl-1-(5,7-difluoro-1,2,3,4-tetrahydro-naphthalen-2-yl)-1,3-dihydroimidazole-2-thione with a primary amide of the formula $H_2NC(O)R^2$ in which $R^2$ is hydrogen, methyl or amino to give a compound of Formula 2 in which $R^2$ is hydrogen, methyl or amino, respectively, or with an ammonium salt of the formula $NH_4+ \ -OC(O)R^3$ is hydrogen or methyl to give a compound of Formula 2 in which $R^2$ is hydrogen or methyl, respectively; preferably wherein 5,7-difluoro-1,2,3,4-tetrahydronaphthalen-2-ylamine is the (S)-isomer thereof.

Processes of the Invention:

The process for making an acid addition salt of a compound of Formula 1 is depicted by the following Reaction Scheme I:

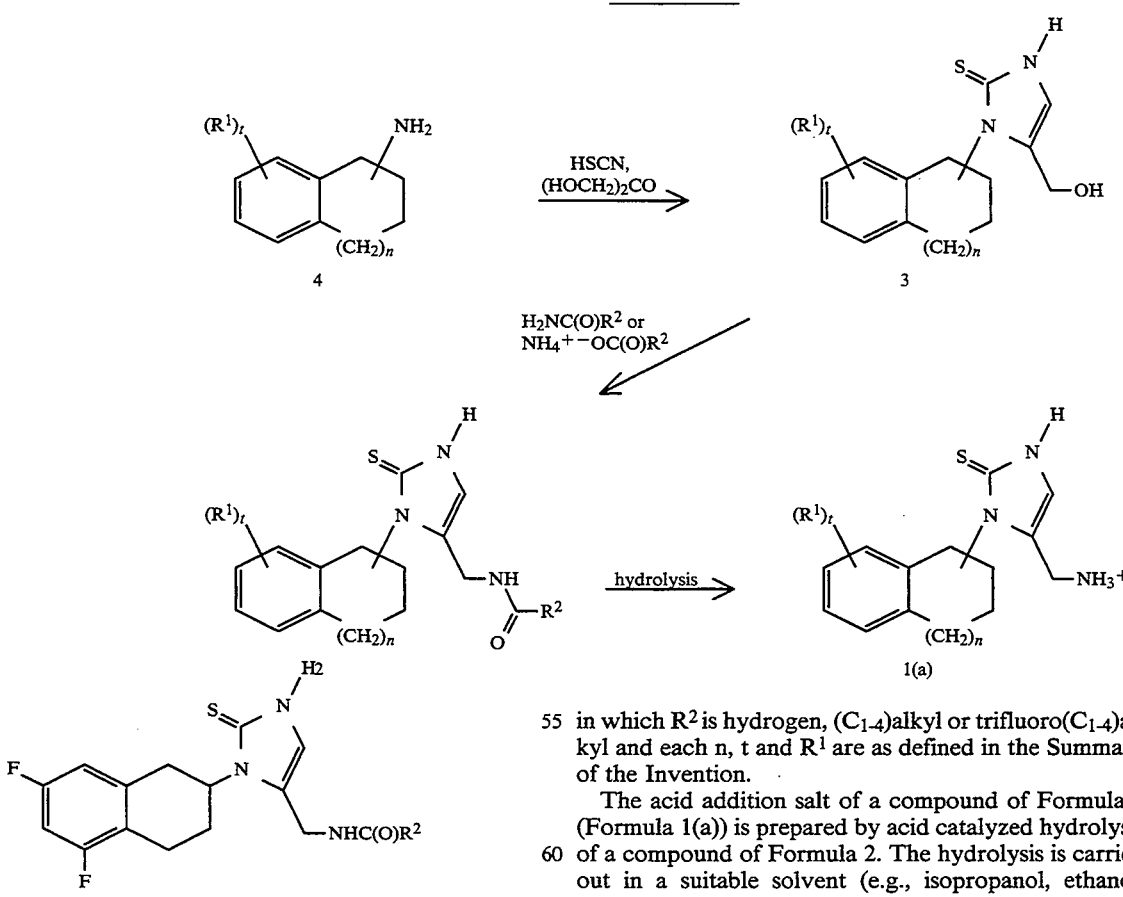

SCHEME I in which $R^2$ is hydrogen, $(C_{1-4})$alkyl or trifluoro$(C_{1-4})$alkyl and each n, t and $R^1$ are as defined in the Summary of the Invention.

The acid addition salt of a compound of Formula 1 (Formula 1(a)) is prepared by acid catalyzed hydrolysis of a compound of Formula 2. The hydrolysis is carried out in a suitable solvent (e.g., isopropanol, ethanol, methanol, etc., preferably isopropanol) and under nitrogen at 65° to 82° C., preferably at reflux temperature, and requires 0.5 to 4 hours. Pharmaceutically acceptable acid addition salts of compounds of Formula 1 can be prepared by performing the hydrolysis with a pharmaceutically acceptable acid (e.g., 2 to 8 equivalents of concentrated hydrochloric acid, preferably approximately 5 equivalents). Alternatively, any acid addition salt form of a compound of Formula 1 can be converted to the corresponding free base form by reacting with an acceptable inorganic or organic base and then converted to a pharmaceutically acceptable acid addition salt by reacting with an appropriate pharmaceutically acceptable acid. The preparation of a compound of Formula 1 as the hydrochloride salt is described in Example 10.

Compounds of Formula 2 in which $R^2$ is hydrogen, $(C_{1-4})$alkyl or trifluoro$(C_{1-4})$alkyl can be prepared by reacting a compound of Formula 3 with a compound of the formula $H_2NC(0)R^2$ (e.g., formamide, acetamide, trifluoroacetamide, etc.). The reaction is carried out by adding the compound of Formula 3 to the amide and then heating the mixture under a stream of nitrogen for 0.5 to 2 hours at 150° to 190° C. Preferably the amide is formamide and the reaction is carried out by heating at 170° to 175° for approximately 1 hour. Proceeding similarly but substituting urea for the primary amide, compounds of Formula 2 in which $R^2$ is amino can be prepared. The preparation of a compound of Formula 2 by the process characterized above is described specifically in Example 8.

Preferably, compounds of Formula 2 in which $R^2$ is hydrogen, $(C_{1-4})$alkyl or trifluoro$(C_{1-4})$alkyl are prepared by reacting a compound of Formula 3 with an ammonium salt of the formula $NH_4+ -OC(0)R^2$ (e.g., ammonium formate, ammonium acetate, ammonium trifluoroacetate, etc., preferably ammonium formate). For example, reacting a compound of Formula 3 with ammonium formate produces a compound of Formula 2 wherein $R^2$ is hydrogen. The reaction is carried out neat or in formamide, preferably in formamide, at 100° to 180° C., preferably at 120° to 150° C., and requires 1 to 2 hours. The preparation of a compound of Formula 2 by the process characterized above is described specifically in Example 9.

Compounds of Formula 3 are prepared by reacting a compound of Formula 4, or the acid addition salt thereof, with thiocyanic acid and dihydroxyacetone in a suitable solvent (e.g., ethyl acetate, THF, dioxane, etc., preferably ethyl acetate) and then optionally treating the reaction mixture with sulfuric acid. The reaction is carried out with potassium thiocyanate in the presence of acid (e.g., glacial acetic acid, propionic acid, etc., preferably glacial acetic acid) under nitrogen at 20° to 50° C. for 0.5 to 3 hours. The treatment with sulfuric acid is not necessary but results in a purer product. The preparation of a compound of Formula 3 is described in Example 7.

A process for making compounds of Formula 4 is depicted by the following Reaction Scheme II:

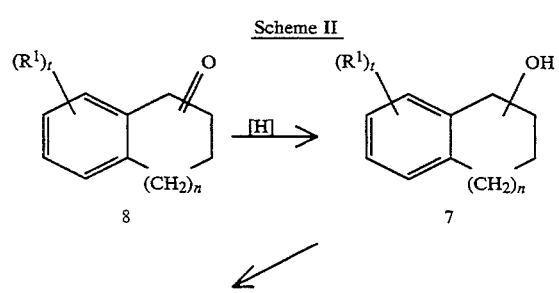

Scheme II

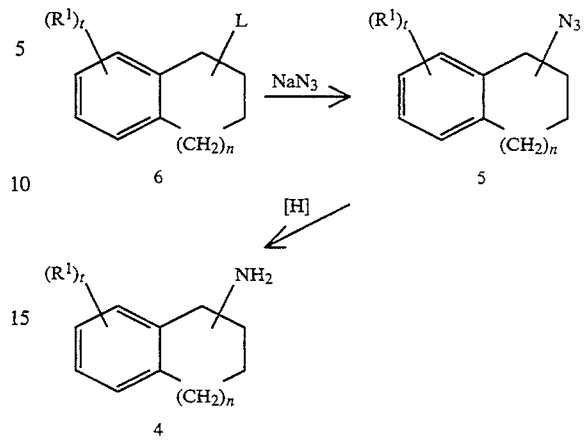

in which L is a leaving group and each n, t and $R^1$ are as defined in the Summary of the Invention.

Compounds of Formula 4 can be prepared by reacting a compound of Formula 6 with an appropriate azide salt (e.g., sodium azide, lithium azide, etc.) in a suitable solvent (e.g., dimethyl sulfoxide (DMSO), N,N-dimethylformamide (DMF), etc.) to give an azide of Formula 5 and then reducing. The reaction with the azide salt is carried out at temperatures of 50° to 90° C., preferably approximately 50° C., and requires 12 to 18 hours. Reduction of the compound of Formula 5 can be effected by catalytic hydrogenation (e.g., $H_2$, 10% palladium on carbon; or $H_2$, platinum on carbon, etc.) in a suitable solvent (e.g., ethyl acetate, ethanol, etc.).

Compounds of Formula 4 can be prepared as an acid addition salt by reacting the free base form of the compound with an inorganic or organic acid in a suitable solvent. For example, a convenient method to prepare the hydrochloride salt of a compound of Formula 4 is by reacting the free base with hydrochloric acid in alcohol.

Compounds of Formula 6 are prepared by treating a compound of Formula 7 with an appropriate agent to create leaving group L. For example, compounds of Formula 6 in which L is mesyloxy can be prepared by reacting a compound of Formula 7 with methanesulfonyl chloride in a suitable solvent (e.g., diethyl ether, tetrahydrofuran (THF), methylene chloride, etc.). The reaction is carried out in the presence of triethylamine at −20° to 5° C., preferably approximately −10° C., and requires 3 to 15 hours.

Compounds of Formula 7 can be prepared by reducing a compound of Formula 8. The reduction is carried out with a chemical reducing agent in a suitable solvent (e.g., sodium borohydride in ethanol, methanol, isopropanol and the like; lithium aluminum hydride (LAH) in diethyl ether, THF, 1,2-dimethoxyethane and the like; etc.) at 0° to 80° C. and requires 1 to 2 hours.

A method for making compounds of Formula 8 in which n is 0 or 1 and the oxo is attached at the d-position is depicted by the following Reaction Scheme III:

Scheme III

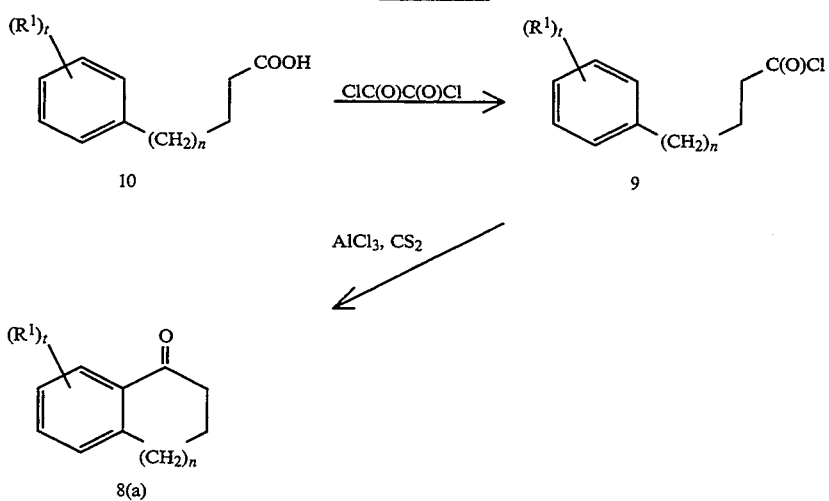

in which each n is 0 or 1 and t and $R^1$ is as defined in the Summary of the Invention.

Compounds of Formula 8 in which n is 0 or 1 and the oxo is attached at the α-position (Formula 8(a)) can be prepared by reacting a compound of Formula 9 with a Lewis acid (e.g., aluminum chloride, aluminum bromide, boron trifluoride, hydrogen fluoride, etc.) in a suitable solvent (e.g., methylene chloride, carbon disulfide, nitrobenzene, etc.). The reaction is carried out in the presence of carbon disulfide at 20° to 45° C., preferably approximately 45° C., and requires 1 to 8 hours.

Compounds of Formula 9 can be prepared by reacting a compound of Formula 10 with a chlorinating agent (e.g., oxalyl chloride, thionylchloride, phosphorus pentachloride, etc., preferably oxalyl chloride) in a suitable solvent (e.g., methylene chloride, dichloroethane, etc.) at 20° to 40° C., preferably approximately 20° C., for 2 to 18 hours.

Compounds of Formula 10 in which n is 0 can be prepared by reacting optionally substituted bromo- or iodobenzene with ethyl acrylate in a suitable solvent (e.g., DMF, dimethylacetamide, DMPU, etc.), reducing and then hydrolyzing. The reaction with the ethyl acrylate is carried out in the presence of a suitable palladium catalyst (e.g., bis(triphenylphosphine palladium(II) chloride) at 70° to 110° C., preferably at approximately 90° C., and requires 4 to 72 hours. The reduction can be effected by catalytic hydrogenation under standard conditions. The hydrolysis can be effected with aqueous base or acid in a suitable solvent (e.g., aqueous sodium hydroxide in ethanol, aqueous sulfuric acid in dioxane, etc.).

Similarly, compounds of Formula 10 in which n is 1 can be prepared by reacting optionally substituted bromo- or iodobenzene with 3-butyn-1-ol in a suitable solvent (e.g., DMF and triethylamine, etc.), reducing and oxidizing. The reaction with the 3-butyn-1-ol is carried out in the presence of a suitable palladium catalyst (e.g., bis(triphenylphosphine palladium(II) chloride) at 80° to 90° C., preferably at approximately 85° C., and requires 4 to 24 hours. The subsequent reduction can be effected by catalytic hydrogenation. The oxidation can be effected with a suitable oxidizing agent (e.g., potassium dichromate(VI), potassium permanganate, etc.).

A method for making compounds of Formula 8 in which n is 1 and the oxo is attached at the β-position is depicted by the following Reaction Scheme IV:

Scheme IV

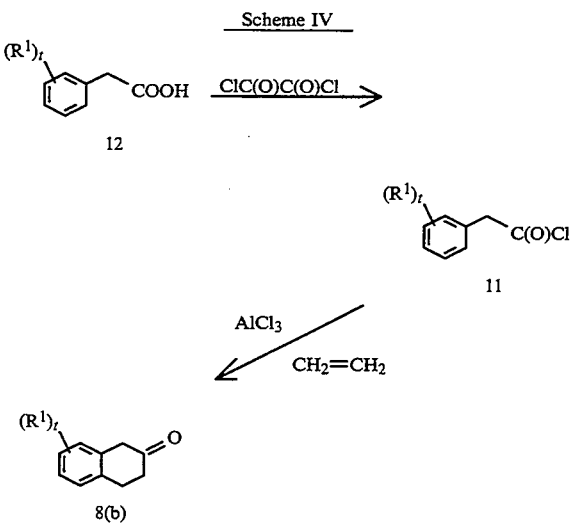

in which each t and $R^1$ is as defined in the Summary of the Invention.

Compounds of Formula 8 in which n is 1 and the oxo is attached at the β-position (Formula 8 (b)) can be prepared by converting a compound of Formula 12 to the corresponding acid chloride (Formula 11) and then reacting the acid chloride with ethylene in the presence of a Lewis acid (e.g., aluminum chloride, boron trifluoride, aluminum bromide, etc.). The conversion to the acid chloride is carried out with an appropriate chlorinating agent (e.g., thionyl chloride, oxalyl chloride, phosphorus pentachloride, etc.) and in a suitable solvent (e.g., methylene chloride, dichloroethane, etc.) at 20° to 40° C., preferably approximately 20° C., and requires 2 to 18 hours. The reaction with ethylene is carried out in a suitable solvent (e.g., methylene chloride, carbondisulfide, etc.) and by adding the acid chloride to the Lewis acid at a rate such that the reaction mixture remains below −40° C., preferably below −60° C., and then bubbling the mixture with ethylene gas for 0.1 to 0.5 hours at −78° to −40° C., preferably approximately −78° C.

A method for making compounds of Formula 8 in which n is 2 and the oxo is attached at the β-position is depicted by the following Reaction Scheme V:

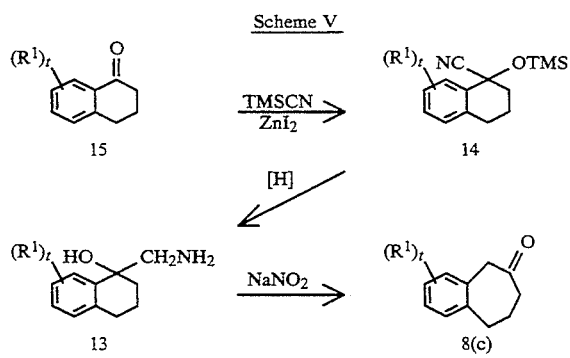

in which each t and R[1] is as defined in the Summary of the Invention.

Compounds of Formula 8 in which n is 2 and the oxo is attached at the β-position (Formula 8(c)] can be prepared by reacting a compound of Formula 13 with sodium nitrite in a suitable solvent (e.g., acetic acid-water, trifluoroacetic acid-water, acetic acid-ethanol, etc.). The reaction is carried out at −15° to 20° C. preferably approximately −5° C. and requires 1 to 18 hours Compounds of Formula 13 are prepared by reacting a compound of Formula 15 with trimethylsilyl cyanide (TMSCN) and zinc chloride neat or in a suitable solvent (e.g., methylene chloride) and then reducing. The reaction with TMSCN is carried out at 0° to 20° C., preferably approximately 20° C., and requires 1 to 18 hours. The reduction can be effected with a chemical reducing agent in a suitable solvent.

A method for making compounds of Formula 8 in which n is 2 and the oxo attached at the γ-position is described by the following Reaction Scheme VI:

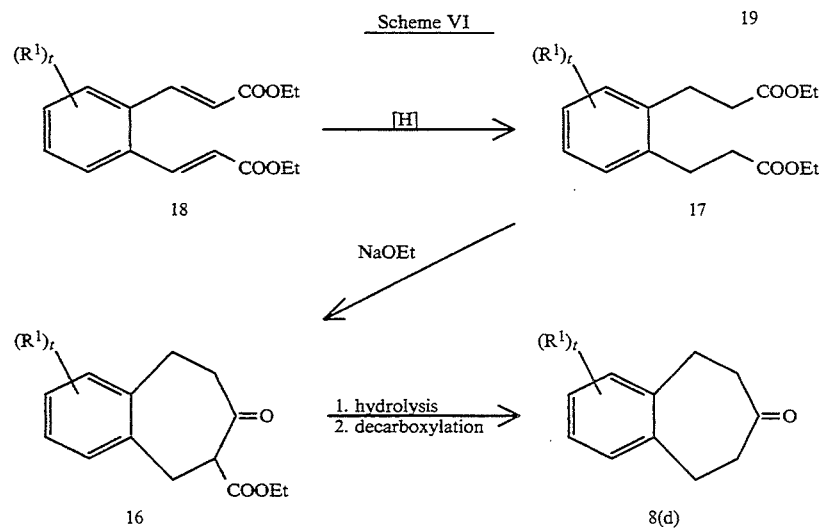

in which each t and R[1] is as defined in the Summary of the Invention.

Compounds of Formula 8 in which n is 2 and the oxo is attached at the γ-position (Formula 8(d)) can be prepared by reacting a compound of Formula 17 with sodium ethoxide in a suitable solvent (e.g., toluene, ethanol, etc.) and then hydrolysis and decarboxylation. The reaction with sodium ethoxide is carried 80° to 110° C., preferably approximately 100° C., and requires 3 to 18 hours. The hydrolysis can be effected by heating in an aqueous base or acid. The decarboxylation can be effected by heating to 80° to 125° C., preferably approximately 100° C, and requires 4 to 8 hours. Compounds of Formula 17 can be prepared by reducing a compound of Formula 18. The reduction can be effected by catalytic hydrogenation (e.g., $H_2$, 10% palladium on carbon, etc.).

Compounds of Formula 18 can be prepared by reacting optionally substituted dibromo or diiodo benzene with ethyl acrylate in a suitable solvent (e.g., DMF, etc.). The reaction with the ethyl acrylate is carried out in the presence of a suitable palladium catalyst (e.g., bis(triphenylphosphine palladium(II) chloride, etc.) at temperatures of 75° to 130° C., preferably at approximately 95° C., and requires 72 to 168 hours.

An alternative method for making compounds of Formula 7 in which n is 0 or 1 and the hydroxy is attached at the β-position is depicted by the following Reaction Scheme VII:

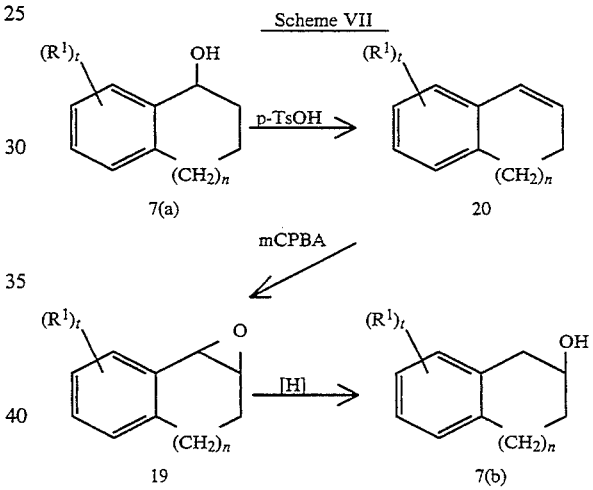

in which each n is 0 or 1 and t and R[1] is as defined in the Summary of the Invention.

Compounds of Formula 7 in which n is 0 or 1 and the hydroxy is attached at the β-position (Formula 7(b)) can be prepared by reacting a compound of Formula 20 with 3-chloroperoxybenzoic acid (m-CPBA) in a suitable solvent (e.g., benzene, methylene chloride, chloroform, etc.) to give an epoxide of Formula 19 and then reducing to give the corresponding β-alcohol. The reaction with m-CPBA is carried out at 0° to 20° C., preferably approximately 0° C., and requires 0.5 to 5 hours. Reduction of the epoxide can be effected by catalytic hydrogenation (e.g., H₂, 10% palladium on carbon; etc.) in a suitable solvent (e.g., ethyl acetate, ethanol, isopropanol, etc.).

Compounds of Formula 20 can be prepared by reacting an α-alcohol of Formula 7(a) with p-toluenesulfonic acid in a suitable solvent (e.g., benzene, toluene, dichloroethane, methylene chloride, etc.) at 20° to 110° C., preferably approximately 80° C., for 1 to 5 hours.

Additional Processes:

Compounds of Formula 1 in which $R^1$ is hydroxy can be prepared by demethylation of the corresponding compound of Formula 1 in which $R^1$ is methoxy. The demethylation is carried out in suitable solvent (e.g., methylene chloride, 1,2-dichloroethane, nitromethane, etc.) at −10° to 20° C., preferably approximately at 0° C., and requires 0.5 to 4 hours.

Compounds of Formula 1 can be prepared as their individual stereoisomers by reacting a racemic mixture thereof with an optically active resolving agent to form a pair of diastereomeric compounds, separating the diastereomers and recoverying the optically pure enatiomer. While resolution of enantiomers can be carried out using covalent diastereomeric derivatives of compounds of Formula 1, dissociable complexes are preferred (e.g., crystalline diastereoisomeric salts). In that compounds of Formula 1 contain a basic amine group, such crystalline diastereoisomeric salts can be prepared by using a suitable optically active acid as the resolving agent (e.g., tartaric acid, mandelic acid, malic acid, the 2-arylpropionic acids in general, camphorsulfonic acid, etc.).

Diastereomers have distinct physical properties (e.g., melting points, boiling points, solubilities, reactivity, etc.) and can be readily separated by taking advantage of these dissimilarities. The diastereomers can be separated by chromatography or, preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixtures can be found in Jean Jacques, Andre Collet, Samuel H. Wilen, Enantiomers, Racemates and Resolutions, john Wiley & Sons, Inc. (1981).

Compounds of Formula 1 can be prepared as their individual stereoisomers from the individual stereoisomers of starting material. The starting material can be prepared as individual stereoisomers by any of the resolution techniques described above or by any method known to one of ordinary skill in the art. For example, compounds of Formula 7 can be prepared as their individual stereoisomers by kinetic enzymatic resolution with a suitable enzyme (e.g., porcine pancreatic lipase, candida cylindracea, pancreatin, etc.).

Alternatively, certain starting materials in the process for preparing compounds of Formula 1 can be prepared as their individual stereoisomers by chiral synthesis. For example, compounds of Formula 7 can be prepared as their individual stereoisomers by chiral reduction of the corresponding compound of Formula 8. Compounds of Formula 7, wherein the hydroxy is attached at the α-position, can be prepared as the (R)-enantiomer by reducing the corresponding compound of Formula 8 with borohydride in the presence of (S)-1-aza-2-boro-3-oxa-4,4-diphenyl[3.3.0]bicyclooctane in THF. Similarly, the (S)-enantiomer can be prepared by reducing the compound of Formula 8 in the presence of (R)-1-aza-2-boro-3-oxa-4,4-diphenyl[3.3.0]bicyclooctane.

Compounds of Formula 7, wherein the hydroxy is attached at the β-position, can be prepared as the (R)-enantiomer by reducing the corresponding compound of Formula 8 with lithium aluminum hydride in the presence of (1R,2S)-N-methylephedrine and 2-ethylaminopyridine. The reaction is carried out in diethyl ether at −78° to −65° C., preferably approximately −78° C., and requires 2 to 3 hours. Similarly, the (S)-enantiomer can be prepared by reducing the compound of Formula 8 in the presence of (1S,2R)-N-methylephedrine and 2-ethylaminopyridine.

Suitable compounds of Formula 8 can be obtained commercially or can be prepared by any of the processes previously described herein or can be prepared by oxidizing an available racemic compound of Formula 7. The oxidation of the racemic compound of Formula 7 can be effected with an appropriate oxidizing agent (e.g., Dess-Martin reagent) in a suitable solvent (e.g., THF, methylene chloride, etc.) at 20° to 50° C.

A preferred method for making a compound of Formula 4 in which n is 1 and the amine is attached at the β-position as the individual (S)-enantiomer is despicted by the following Reaction Scheme VIII:

SCHEME VIII

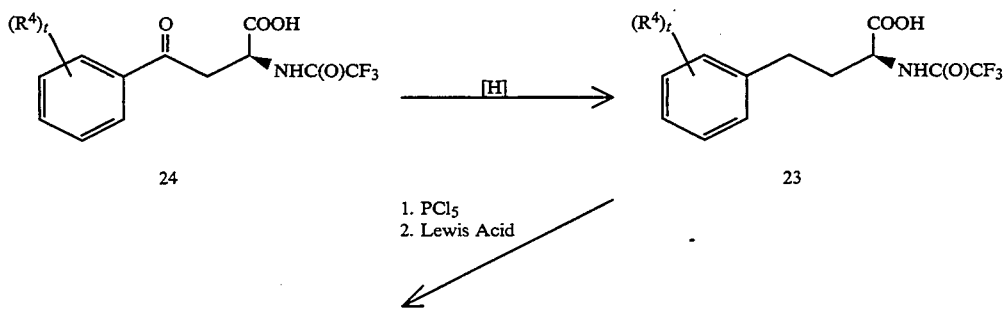

-continued
SCHEME VIII

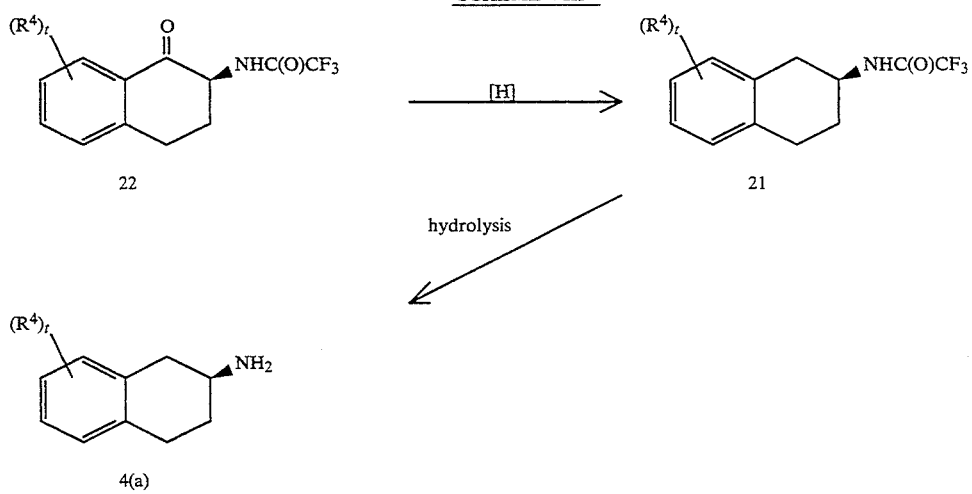

in which each t and $R^1$ are as defined in the Summary of the Invention. Compounds of Formula 4 in which n is 1 and the amine is attached at the β-position can be prepared as the individual (S)-enantiomer (Formula 4(a)) by hydrolyzing a compound of Formula 21. The hydrolysis can be carried out with an aqueous base (e.g., lithium hydroxide monohydrate, sodium hydroxide, potassium hydroxide potassium carbonate, etc., preferably lithium hydroxide monohydrate) in a suitable solvent (e.g., methanol, ethanol, isopropanol, etc., preferably methanol) at 25° to 100° C., preferably reflux temperature, and requires 0.5 to 5 hours. The preparation of a compound of Formula 4 is described in Example 6.

Compounds of Formula 21 are prepared by hydrogenolysis of a compound of Formula 22. The hydrogenolysis can be accomplished by a two step process comprising (i) hydrogenating a compound of Formula 22 until conversion to the corresponding 1-naphthol is complete and (ii) adding sulfuric acid and continuing hydrogenation to give the compound of Formula 21. Hydrogenation of the compound of Formula 22 to a 1-naphthol is carried out in the presence of an appropriate catalyst (e.g., Pearlman's catalyst, palladium on carbon, etc., preferably Pearlman's catalyst) in acetic acid or trifluoroacetic acid (TFA), preferably acetic acid, at 1 to 130 psig and 10° to 30° C. and requires 0.5 to 4 hours. Hydrogenation of the 1-naphthol is carried out by adding 1 to 10 equivalents, preferably 4 to 6 equivalents, of sulfuric acid or perchloric acid and continuing the hydrogenation under the same conditions for 3 to 120 hours. Alternatively, the hydrogenolysis is effected by a single step process comprising hydrogenating the compound 10 in the presence of an appropriate catalyst and either sulfuric acid or perchloric acid in acetic acid. The single step hydrogenolysis is carried out at 1 to 130 psig and 10° to 30° C. and requires 3 to 120 hours. The preparation of a compound of Formula 21 is described in Example 5.

Compounds of Formula 22 are prepared from compounds of Formula 23 by an intramolecular Friedel-Crafts reaction. The reaction is effected by converting a compound 23 to the corresponding acid chloride and then treating the acid chloride with an appropriate Lewis acid (e.g. aluminum chloride, hydrogen fluoride, etc., preferably aluminum chloride). Conversion to the acid chloride can be carried out with an appropriate chlorinating agent (e.g., phosphorus pentachloride, thionyl chloride, oxalyl chloride, etc., preferably phosphorus pentachloride) in methylene chloride at 0° to 10° C., preferably at 5° to 10° C., and requires 0.5 to 2 hours. The treatment with Lewis acid and the resultant ring closure is carried out at 0° to 10° C., preferably at 5° to 10° C., and requires 1 to 3 hours. Preferably, the crude product is isolated by crystallization from a methanol/water or isopropanol/water mixture; and then, if necessary, recrystallization from a toluene/heptane mixture. The preparation of a compound of Formula 22 is described in Example 4.

Compounds of Formula 23 are prepared by hydrogenolysis of a compound of Formula 24. The hydrogenolysis is carried out by hydrogenating in the presence of an appropriate catalyst (e.g., 20% palladium hydroxide on carbon (Pearlman's catalyst), palladium on carbon, etc., preferably Pearlman's catalyst) and 1 to 5 equivalents, preferably 1.5 to 2 equivalents, of sulfuric acid, in a glacial acetic acid at 1 to 60 psig and 5° to 30° C. and requires 2 to 48 hours. The preparation of a compound of Formula 23 is described in Example 3.

Compounds of Formula 24 are prepared via a Friedel-Crafts alkylation of optionally substituted benzene with N-(trifluoroacetyl)-L-aspartic anhydride. The alkylation is carried out in the presence of a Lewis acid (e.g., aluminum chloride, tin chloride, hydrogen fluoride, etc., preferably aluminum chloride) and in a suitable solvent (e.g., methylene chloride, etc., preferably methylene chloride) at 25° to 40° C., preferably at reflux temperature, and requires 2 to 5 hours. The preparation of a compound of Formula 24 is described in Example 2.

N-(Trifluoroacetyl)-L-aspartic anhydride is prepared by reacting L-aspartic acid with trifluoroacetic anhydride (TFAA). The reaction is highly exothermic and when more than 100 g amounts of reactants are employed, it must be conducted under conditions such that the liberation of heat is controlled. For example, a convenient method for carrying out the reaction is by heating 2 to 4 equivalents, preferably 2.3 to 2.5 equivalents, of TFAA to between 30° and 40° C., preferably to reflux temperature, and then adding 1 equivalent of L-aspartic acid at a rate such that the reaction readily proceeds but the heat generated by the reaction can be dissipated by reflux. Preferably the L-aspartic acid is added to the TFAA as a solution in TFA over 30 to 60 minutes. The preparation of N-(trifluoroacetyl)-L- aspartic anhydride is described specifically in Example 1.

Similarly, the (R)-enantiomer of a compound of Formula 4 in which n is 1 can be prepared by proceeding as described in Reaction Scheme VIII but substituting D-aspartic acid for L-aspartic acid.

EXAMPLE 1

N-(Trifluoroacetyl)-L-aspartic Anhydride

Trifluoroacetic anhydride (7.7 kg, 5.3 L, 37.5 mol) was heated to reflux temperature and a solution of L-aspartic acid (2.0 kg, 15.0 mol) in 9 L of trifluoroacetic acid (prepared by gradually heating to 65° C. and stirring for 3 hours) was added to the refluxing trifluoroacetic anhydride over 30 minutes. The mixture then was distilled and 9 L of trifluoroacetic acid was removed. The remaining mixture was added to 8 L of cold, hexane under nitrogen. The hexane mixture was stirred for 3 hours in an ice bath giving a crystalline material. The material was isolated by filtration and the filter residue was washed with approximately 25 L of hexane. Drying to constant weight in a vacuum oven at 50° C. under a nitrogen gas bleed gave N-(trifluoroacetyl)-L-aspartic anhydride (2.9 kg, 13.7 mol), m.p. 140°–141° C. $[\alpha]_D$ −27.4° (c=3.28, THF).

EXAMPLE 2

(S)-2-[(Trifluoroacetyl)amino]-4-(2,4-difluorophenyl)-4-oxobutanoic acid

The following is the preparation of a compound of Formula 24 in which n is 1, t is 2 and $R^1$ is fluoro at the 2- and 4-position.

A solution of 1,3-difluorobenzene (2.3 kg, 20.0 mol) in 5 L of methylene chloride was added to a mixture of N-(trifluoroacetyl)-L-aspartic anhydride (4.2 kg, 20.0 mol), prepared as in Example 1, and aluminum chloride (7.4 kg, 55.5 mol) in 25 L of methylene chloride. The temperature of the reaction mixture was increased gradually over 1.5 hours and held at reflux for an additional 3 hours. The mixture then was cooled and 10 L of water and 20 L of 6N hydrochloric acid were added with good agitation. The methylene chloride layer was separated, washed with water and then brine, and the volatiles were removed by distilling at atmospheric pressure.

The residue was dissolved in 40 L of toluene and 8 L of volatiles was removed by distilling the mixture in vacuo. The solution was heated to 50° C. and 8 L of hexane was added. The mixture was cooled to 30° C. and 90 L of hexane was added. The mixture then was stirred at 25° C. for 3 hours giving a crystalline material. The material was isolated by filtration and the filter residue was washed with hexane (3×10 L). Drying to a constant weight in a vacuum oven at room temperature under a nitrogen bleed gave (S)-2-[(trifluoroacetyl)amino]-4-(2,4-difluorophenyl)-4-oxobutanoic acid (5.2 kg, 16.0 mol), m.p. 82.4°–84.0° C. $[\alpha]_D$+15.2° (c=0.956, CH$_3$OH).

EXAMPLE 3

(S)-2-[(Trifluoroacetyl)amino]-4-(2,4-difluorophenyl)-butanoic acid

The following is the preparation of a compound of Formula 23 in which n is 1, t is 2 and $R^1$ is fluoro at the 2- and 4-position.

A mixture of (S)-2-[(trifluoroacetyl)amino]-4-(2,4-difluorophenyl)-4-oxobutanoic acid (4.8 kg, 14.7 mol), prepared as in Example 2, and activated carbon, Darco®, (0.4 kg) in 5 L of acetic acid was stirred at room temperature for 1 hour. The mixture was filtered on to Pearlman's catalyst (0.5 kg, 50% wet) and washed in with 15 L of glacial acetic acid. Sulfuric acid (1.2 L, 21.8 mol) in 1 L of glacial acetic acid was filtered into the mixture and washed in with 2.8 L of glacial acetic acid. The reaction vessel was vacuum/pressure purged 3 times with nitrogen and then 6 times with hydrogen to 10 psig. The mixture was stirred vigorously under hydrogen at atmospheric pressure at room temperature, for 24 hours. The reaction vessel then was purged with nitrogen and the mixture was filtered onto 4.6 kg of sodium acetate trihydrate. The filter was washed with 10 L of glacial acetic acid. The glacial acetic acid was removed by distilling the mixture in vacuo.

The residue was partitioned between 20 L of methylene chloride and 40 L of water. The aqueous layer was extracted with 10 L of methylene chloride and the combined methylene chloride was washed with 10 L of water. The methylene chloride mixture then was dried over sodium sulfate (10 kg) and filtered. The solvent was removed in vacuo and the residue was dissolved in 5 L of methylene chloride. The solution was added under nitrogen to 15 L of hexane at a rate such that the temperature of the hexane mixture remained between 0° and 5° C. The mixture was allowed to stand for 1 hour giving a crystalline material. The material was isolated by filtration and the filter residue was washed with 10 L of hexane. Drying to constant weight in vacuo at 25° C. with a nitrogen bleed gave (S)-2-[(trifluoroacetyl)amino]-4-(2,4-difluorophenyl)butanoic acid (3.3 kg, 10.4 mol), m.p. 62°–83.5° C. An analytically pure sample had a melting point of 86°–89° C. $[\alpha]_D$+6.8° (c=0.995, CH$_3$OH).

EXAMPLE 4

(S)-5,7-Difluoro-2-[(trifluoroacetyl)amino]-3,4-dihydro-1(2H)-naphthalenone

The following is the preparation of a compound of Formula 22 in which n is 1, t is 2 and $R^1$ is fluoro at the 5- and 7-position.

A suspension of phosphorus pentachloride (2.2 kg, 10.6 mol) in 12 L of methylene chloride was cooled to 5° C. and (S)-4-(2,4-difluorophenyl)-2-[(trifluoroacetyl)amino]butanoic acid (3.1 kg, 9.9 mol), prepared as in Example 3, in 12 L of methylene chloride was added over 20 minutes. Thin layer chromatography of a methanol-quenched aliquot confirmed that the butanoic acid had converted to the corresponding acid chloride.

The mixture was stirred for 30 minutes and then was added to a slurry of aluminum chloride (4.3 kg) in 38.8 L of methylene chloride at a rate such that the temperature of the slurry remained between 1° and 5° C. The reaction mixture was stirred for 1 hour and then added to 28 kg of ice and 5.3 kg of concentrated hydrochloric acid. The mixture was stirred for 1 hour and the temperature allowed to rise to 20° C.

The aqueous layer was separated and extracted methylene chloride (2×15 L). The methylene chloride layer was washed once with water and combined with the methylene chloride extracts. The combined methylene chloride then was washed with water. The pH of the aqueous phase was adjusted to 6 by addition of aqueous sodium bicarbonate solution. The methylene chloride layer was washed with water and then brine. The methylene chloride was dried over sodium sulfate and filtered. The mixture was concentrated by evaporation at atmospheric pressure and the residue was dissolved in 15 L of methanol. The methanol solution was distilled to remove residual methylene chloride and then 9.9 L of water was added. The mixture was warmed to 56° C., allowed to cool to room temperature and then stirred for approximately 12 hours. A crystalline material was obtained and isolated by filtration. The filter residue was washed with 15 L of water. The isolated material was dried to constant weight in vacuo at room temperature with a nitrogen bleed.

The material was dissolved in 5 L of toluene at a temperature of 90° C. and combined with 10 L of heptane at a temperature of 80° C. The temperature of the mixture gradually was decreased over 1.5 hours. The mixture then was stirred at 5° C. for approximately 12 hours giving a crystalline material. The material was isolated by filtration and the filter residue was washed with 15 L of heptane. Drying to constant weight in vacuo at room temperature with a nitrogen bleed gave (S)-5,7-difluoro-2-[(trifluoroacetyl)amino]-3,4-dihydro(2H)-naphthalen-1-one (2.0 kg, 6.8 mol), m.p. 142.4°–144.6° C. $[\alpha]_D-59.4°$ (c=0.994, CH$_3$OH).

EXAMPLE 5

(S)-5,7-Difluoro-2-[(trifluoroacetyl)amino]-1,2,3,4-tetrahydronaphthalene

The following is the preparation of a compound of Formula 21 in which n is 1, t is 2 and R$^1$ is fluoro at the 5- and 7-position.

A reaction vessel containing a mixture of (S)-5,7-difluoro-2-[(trifluoroacetyl)amino]-3,4-dihydro-(2H)-naphthalen-1-one (1.1 kg, 3.8 mol), prepared as in Example 4, and Pearlman's catalyst (0.55 kg, 50% wet) in 11 L of TFA was vacuum/pressure purged 8 times with nitrogen and then 8 times with hydrogen to 11 psig. The mixture was stirred vigorously under hydrogen (125 psig) at room temperature for 24 hours. Thin layer chromatography confirmed that the naphthalen-1-one had converted to (S)-1-hydroxy-5,7-difluoro-2-[(trifluoroacetyl)amino]-3,4-dihydro-(2H)-naphthalene.

Sulfuric acid (1.1 L, 19.4 mol) in 1 L of TFA then was added and the mixture stirred under hydrogen (125 psig) at room temperature for an additional 24 hours. The reaction vessel then was purged with nitrogen and the mixture was filtered over celite and washed through with 11 L of TFA. The filtrate was combined with 2.8 kg sodium acetate trihydrate and 80 L of water. The mixture was cooled to 10° C. giving a crystalline material. The material was isolated by filtration and the filter residue was washed with 10 L of ice water. Drying gave (S)-5,7-difluoro-2-[(trifluoroacetyl)amino]-1,2,3,4-tetrahydronaphthalene (0.8 kg, 2.9 mol), m.p. 159.9°–160.9° C. $[\alpha]_D-56.0°$ (c=1.01, CH$_3$OH).

EXAMPLE 6

(S)-5,7-Difluoro-1,2,3,4-tetrahydronaphthalen-2-ylamine Hydrochloride

The following is the preparation of a compound of Formula 4 in which n is 1, t is 2 and R$^1$ is fluoro at the 5- and 7-position.

Lithium hydroxide monohydrate (7.8 g, 0.2 mol) was added to a solution of (S)-5,7-difluoro-2-[(trifluoroacetyl)amino]-1,2,3,4-tetrahydronaphthalene (20.8 g, 74.5 mmol), prepared as in Example 5, in 187 mL of methanol and 21 mL of water. The mixture was stirred at reflux for 30 minutes and diluted with 200 mL of methanol. The diluted mixture then was combined with 60 mL of water, 24.8 mL of concentrated hydrochloric acid and 4.2 g of activated carbon, Darco®. The mixture was stirred for 30 minutes and then filtered through celite. The filtrate was distilled until the head temperature reached 75° C. The remaining mixture was allowed to cool and let stand for approximately 60 hours. The mixture then was cooled in an ice bath giving a crystalline material. The material was isolated by filtration and the filter residue was washed with water. Drying to constant weight in vacuo at room temperature under a nitrogen stream gave (S)-5,7-difluoro-1,2,3,4-tetrahydronaphthalen-2-ylamine hydrochloride (14.8 g, 67.6 mol), m.p. >280° C. $[\alpha]_D-66.2°$ (c=0.162, CH$_3$OH).

EXAMPLE 7

(S)-5-Hydroxymethyl-1-(5,7-difluoro-1,2,3,4-tetrahydronaphthalen-2-yl)-1,3-dihydroimidazole-2-thione The following is the preparation of a compound of Formula 3 in which n is 1, t is 2 and R$^1$ is fluoro at the 5- and 7-position.

Potassium thiocyanate (15.9 g, 162.6 mmol) was dried by heating to 175° C. under nitrogen and then cooled to 35° C. under vacuum with several nitrogen purges. A mixture of dihydroxyacetone (15.9 g, 176.7 mmol) and (S)-5,7-difluoro-1,2,3,4-tetrahydronaphthalen-2-ylamine hydrochloride (30.0 g, 137.0 mmol), prepared as in Example 6, in 540 mL of ethyl acetate was added to the dry potassium thiocyanate. The reaction vessel was purged with nitrogen and 40.83 g of glacial acetic acid was added. The reaction mixture was stirred at 35° C. for 2 hours and 100 mL of 1.0M sulfuric acid was added. The mixture was stirred for 15 minutes, then cooled in an ice bath and 2.5M sodium hydroxide was added until the mixture was pH 7. The organic layer was washed with 50 mL of saturated aqueous sodium bicarbonate and then 50 mL of brine. The organic layer was concentrated to 480 mL by distillation and the mixture was cooled to 6° C. and allowed to stand for 12 hours giving a crystalline material. The material was isolated by filtration, the filter residue was washed with cold ethyl acetate and the isolated material dried.

The material was dissolved in 650 mL of ethyl acetate and 25 mL of water. The mixture was distilled until 500 mL of volatiles were removed. The mixture was cooled to room temperature and stirred for 45 minutes giving a crystalline material. The material was isolated by filtration and the filter residue was washed with cold ethyl acetate. Drying in vacuo with a nitrogen bleed gave (S)-5-hydroxymethyl-1-(5,7-difluoro-1,2,3,4-tetrahydronaphthalen-2-yl)-1,3-dihydroimidazole-2-thione (30.4 g, 107.4 mol), m.p. 206°–207° C. $[\alpha]_D-40°$ (c=0.682, CH$_3$OH).

EXAMPLE 8

(S)-N-[3-(5,7-Difluoro-1,2,3,4-tetrahydronaphthalen-2-yl)-2-thioxo-2,3-dihydro-1H-imidazol-4-ylmethyl]formamide The following is the preparation of a compound of Formula 2 in which n is 1, t is 2, R$^1$ is fluoro at the 5- and 7-position and R$^2$ is hydrogen.

Formamide (250 mL, 6.3 mol) was heated to 175° and (S)-5-hydroxymethyl-1-(5,7-difluoro-1,2,3,4-tetrahydronaphthalen-2-yl)-1,3-dihydroimidazole-2-thione (25.0 g, 88.3 mmol), prepared as in Example 7, was added in portions over 30 minutes and the reaction mixture was stirred for 1 hour under a nitrogen sweep. The mixture was cooled to 50° C. and 2.5 g of activated carbon, Darco ®, was added. The mixture was cooled to 30° C., filtered through celite and washed in with 25 mL of formamide. The filtrate was heated to 95° C. and then 1 L of water was added dropwise. The mixture was allowed to cool and then stirred at room temperature for 12 hours. The mixture was cooled to 0° C. giving a crystalline material. The material was isolated by filtration and dried.

The material was stirred with approximately 5 times by weight of 70% THF/30% hexanes for five minutes. The material was isolated by filtration and the filter residue was washed with 50% THF/50% hexanes. Drying to constant weight gave (S)-N-[3-(5,7-difluoro-1,2,3,4-tetrahydronaphthalen-2-yl)-2-thioxo-2,3-dihydro-1H-imidazol-4-ylmethyl]formamide (19.5 g, 62.7 retool), m.p. 245°–246° C. $[\alpha]_D+48.9°$ (c=0.613, DMSO).

Proceeding similarly as in Example 18, but subsituting urea for formamide (S)-5-ureidomethyl-1-(5,7-difluoro-1,2,3,4-tetrahydro-naphthalen-2-yl)-1,3-dihydroimidazole-2-thione, m.p. 258°–260° C., $[\alpha]_D+34.3°$ (c=0.574, DMSO).

EXAMPLE 9

(S)-N-[3-(5,7-Difluoro-1,2,3,4-tetrahydronaphthalen-2-yl)-2-thioxo-2,3-dihydro-1H-imidazol-4-ylmethyl]formamide The following is the preparation of a compound of Formula 2 in which n is 1, t is 2, $R^1$ is fluoro at the 5- and 7-position and $R^2$ is hydrogen.

A mixture of (S)-5-hydroxymethyl-1-(5,7-difluoro-1,2,3,4-tetrahydronaphthalen-2-yl)-1,3-dihydroimidazole-2-thione (1.0 g, 3.5 mmol), prepared as in Example 7, and ammonium formate (10 g, 158.6 mmol) stirred at approximately 125° C. for 1 hour. The mixture was then heated to approximately 138° C. and stirred for an additional 35 minutes. The mixture was diluted with 25 mL of water and allowed to cool to room temperature. The mixture was aged for approximately 18 hours giving a crystalline material. The material was isolated by filtration and the filter residue was washed with water. Drying to constant weight gave (S)-N-[3-(5,7-difluoro-1,2,3,4-tetrahydronaphthalen-2-yl)-2-thioxo-2,3-dihydro-1H-imidazol-4-ylmethyl]formamide (0.92 g, 2.96 mmol).

Proceeding similarly as in Example 9, but substituting ammonium acetate for ammonium formate gave (S)-N-[3-(5,7-difluoro-1,2,3,4-tetrahydronaphthalen-2-yl)-2-thioxo-2,3-dihydro-1H-imidazol-4-ylmethylacetamide, m.p. 275.5°–276(dec)° C. $[\alpha]_D+41.3°$ (c=1.00, DMSO).

EXAMPLE 10

(S)-5-Aminomethyl-1-(5,7,difluoro-1,2,3,4-tetrahydronaphthalen-2-yl)-2,3-dihydro-2-thioxo-1H-imidazole Hydrochloride The following is the preparation of a compound of Formula 1 in which n is 1, t is 2 and $R^1$ is fluoro at the 5- and 7-position.

A mixture of (S)-N-[3-(5,7-difluoro-1,2,3,4-tetrahydronaphthalen-2-yl)-2-thioxo-2,3-dihydro-1H-imidazol-4-ylmethyl]formamide (19.1 g, 59.0 mmol), prepared as in Example 8, and 25 mL of concentrated hydrochloric acid (12.0M, 25 mL, 300 mmol) in 400 mL of isopropanol was heated to reflux over 12 minutes and stirred for 1 hour 40 minutes. The mixture was distilled removing 150 mL of isopropanol. The mixture was gradually cooled to room temperature and stirred for 3 hours 45 minutes. The material was isolated by filtration and the filter residue was washed with 75 mL of isopropanol. Drying in vacuo at 110° to 125° C. with a nitrogen bleed gave (S)-5-aminomethyl-1-(5,7-difluoro-1,2,3,4-tetrahydronaphthalen-2-yl)-1,3-dihydroimidazole-2-thione hydrochloride (15.6 g, 47.1 mmol), m.p. 251.9° C. $[\alpha]_D+10.2°$ (c=0.500, DMSO).

We claim:

1. A process for the preparation of an acid addition salt of a compound of Formula 1:

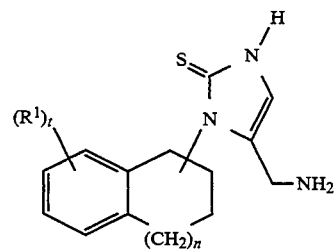

in which:

n is 0, 1 or 2;

t is 0, 1, 2 or 3;

$R^1$ is independently halo, hydroxy or $(C_{1-4})$alkyloxy; or the free base, an individual stereoisomer, or a mixture of stereoisomers thereof; which process comprises:

(A) reacting a compound of Formula 4:

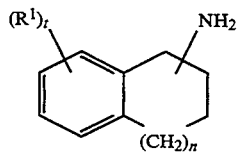

in which n, t and $R^1$ are as defined above, with thiocyanic acid and dihydroxyacetone to give a compound of Formula 3:

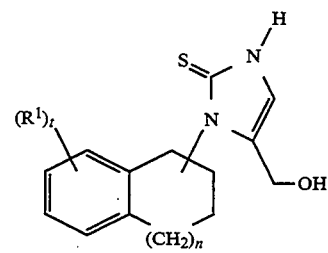

in which n, t and $R^1$ are as defined above;

(B) reacting the compound of Formula 3 with a compound of the formula $H_2NC(O)R^2$ or an ammonium salt of the formula $NH_4+ -OC(O)R^2$ (in which $R^2$ is hydrogen, $(C_{1-4})$alkyl or trifluoro$(C_{1-4})$alkyl) to give a compound of Formula 2:

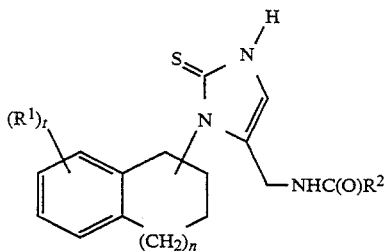

in which n, t, $R^1$ and $R^2$ are as defined above; and (C) hydrolyzing the compound of Formula 2 with acid; and (D) optionally reacting the acid addition salt form of a compound of Formula 1 with an inorganic or organic base to give the corresponding free base form; and (E) optionally reacting the free base form of a compound of Formula 1 with a pharmaceutically acceptable acid to give the corresponding acid addition salt; and (F) optionally separating a mixture of stereoisomers of a compound of Formula 1 to give a single stereoisomer.

2. A process for the preparation of an acid addition salt of a compound of Formula 1:

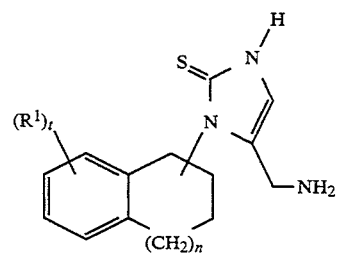

in which:
n is 0, 1 or 2;
t is 0, 1, 2 or 3;
$R^1$ is independently halo, hydroxy or $(C_{1-4})$alkyloxy;
or the free base, an individual stereoisomer, or a mixture of stereoisomers thereof; which process comprises:

(A) reacting a compound of Formula 3:

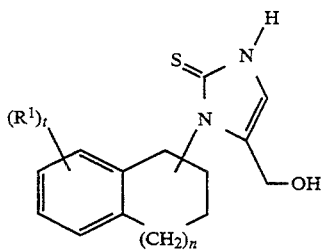

in which n, t and $R^1$ are as defined above, with a compound of the formula $H_2NC(O)R^2$ or an ammonium salt of the formula $NH_4^+ -OC(O)R^2$ in which is $R^2$ is hydrogen, $(C_{1-4})$alkyl or trifluoro$(C_{1-4})$alkyl) to give a compound of Formula 2:

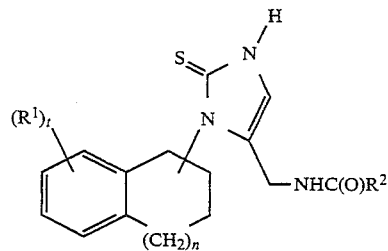

in which n, t and $R^1$ are as defined above; and (B) hydrolyzing the compound of Formula 2 with acid; and (C) optionally reacting the acid addition salt form of a compound of Formula 1 with an inorganic or organic base to give the corresponding free base form; and (D) optionally reacting the free base form of a compound of Formula 1 with a pharmaceutically acceptable acid to give the corresponding acid addition salt; and (E) optionally separating a mixture of stereoisomers of a compound of Formula 1 to give a single stereoisomer.

3. A process for the preparation of an acid addition salt of 5-aminomethyl-1-(5,7-difluoro-1,2,3,4-tetrahydronaphthalen-2-yl)-1,3-dihydroimidazole-2-thione or the free base, individual stereoisomer, or a mixture of stereoisomers thereof; which process comprises:

(A) reacting 5,7-difluoro-1,2,3,4-tetrahydronaphthalen-2-ylamine with thiocyanic acid and dihydroxyacetone to give 5-hydroxymethyl-1-(5,7-difluoro-1,2,3,4-tetrahydronaphthalen-2-yl)-1,3-dihydroimidazole-2-thione;

(B) reacting the 5-hydroxymethyl-1- (5,7-difluoro-1,2,3,4-tetrahydronaphthalen-2-yl)-1,3-dihydroimidazole-2-thione with a compound of the formula $H_2NC(O)R^2$ or an ammonium salt of the formula $NH_4+ -OC(0)R^2$ (in which $R^2$ is hydrogen, $(C_{1-4})$alkyl or trifluoro$(C_{1-4})$alkyl) to give a compound of Formula 2 (a):

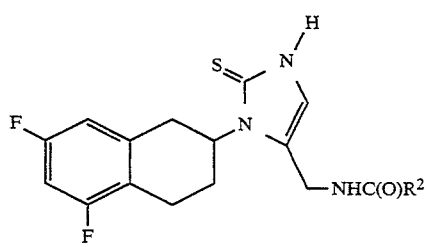

in which $R^2$ is as defined above; and (C) hydrolyzing the compound of Formula 2(a) with acid; and (D) optionally reacting the acid addition salt form of 5-aminomethyl-1-(5,7-difluoro-1,2,3,4-tetrahydronaphthalen-2-yl)-1,3-dihydroimidazole-2-thione with an inorganic or organic base to give the corresponding free base form; and (E) optionally reacting the free base form of 5-aminomethyl-1-(5,7-difluoro-1,2,3,4-tetrahydronaphthalen-2-yl)-1,3-dihydroimidazole-2-thione with a pharmaceutically acceptable acid to give the corresponding acid addition salt; and (F) optionally separating a mixture of stereoisomers of 5-aminomethyl-1-(5,7-difluoro-1,2,3,4-tetrahydronaphthalen-2-yl)-1,3-dihydroimidazole-2-thione to give a single stereoisomer.

4. The process of claim 3 in which the 5,7-difluoro-1,2,3,4-tetrahydronaphthalen-2-ylamine is the (S)-isomer thereof.

5. The process of claim 4 in which R² is hydrogen.

6. The process of claim 5 in which the compound of Formula 3 is reacted with ammonium formate.

7. The process of claim 6 in which the compound of Formula 2(a) is hydrolyzed with hydrochloric acid to give (S)-5-aminomethyl-1-(5,7-difluoro-1,2,3,4-tetrahydronaphthalen-2-yl)-1,3-dihydroimidazole-2-thione hydrochloride.

8. A process for the preparation of an acid addition salt of 5-aminomethyl-1-(5,7-difluoro-1,2,3,4-tetrahydronaphthalen-2-yl)-1,3-dihydroimidazole-2-thione or the free base, an individual stereoisomer, or a mixture of stereoisomers thereof; which process comprises:

(A) reacting 5-hydroxymethyl-1-(5,7-difluoro-1,2,3,4-tetrahydronaphthalen-2-yl)-1,3-dihydroimidazole-2-thione with a compound of the formula H₂NC(0)R² or an ammonium salt of the formula NH₄+ −OC(0)R² (in which R² is hydrogen, (C₁₋₄)alkyl or trifluoro(C₁₋₄)alkyl) to give a compound of Formula 2(a):

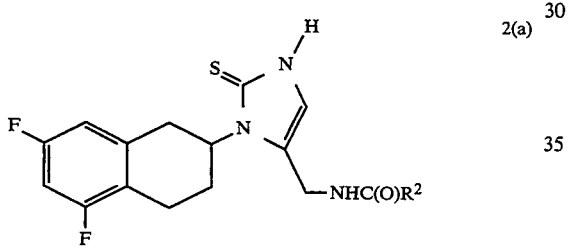

in which R² is as defined above; and (B) hydrolyzing the compound of Formula 2(a) with acid; and (C) optionally reacting the acid addition salt form of 5-aminomethyl-1-(5,7-difluoro-1,2,3,4-tetrahydronaphthalen-2-yl)-1,3-dihydroimidazole-2-thione with an inorganic or organic base to give the corresponding free base form; and (D) optionally reacting the free base form of 5-aminomethyl-1-(5,7-difluoro-1,2,3,4-tetrahydronaphthalen-2-yl)-1,3-dihydroimidazole-2-thione with a pharmaceutically acceptable acid to give the corresponding acid addition salt; and (E) optionally separating a mixture of stereoisomers of 5-aminomethyl-1-(5,7-difluoro-1,2,3,4-tetrahydronaphthalen-2-yl)-1,3-dihydroimidazole-2-thione to give a single stereoisomer.

9. The process of claim 8 in which the compound of Formula 2(a) is the (S)-isomer thereof.

10. The process of claim 9 in which R² is hydrogen.

11. The process of claim 10 in which the compound of Formula 2(a) is hydrolyzed with hydrochloric acid to give (S)-5-aminomethyl-1-(5,7-difluoro-1,2,3,4-tetrahydronaphthalen-2-yl)-1,3-dihydroimidazole-2-thione hydrochloride.

12. A process for the preparation of a compound of Formula 2:

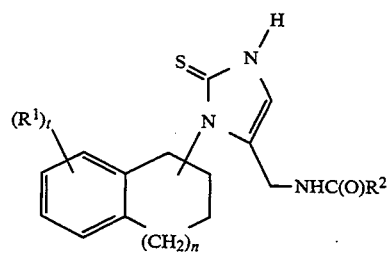

in which:

n is 0, 1 or 2;

t is 0, 1, 2 or 3;

R¹ is independently halo, hydroxy or (C₁₋₄)alkyloxy; and

R² is hydrogen, amino, (C₁₋₄) alkyl or trifluoro (C₁₋₄)alkyl; or the individual stereoisomers, or a mixture of stereoisomers thereof; which process comprises:

(A) reacting a compound of Formula 4 :

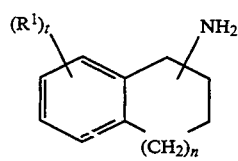

in which n, t and R¹ are as defined above, with thiocyanic acid and dihydroxyacetone to give a compound of Formula 3:

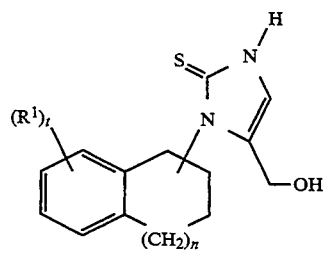

in which n, t and R¹ are as defined above; and (B) reacting the compound of Formula 3 with a primary amide of the formula H₂NC(0)R² in which R² is as defined above to give a compound of Formula 2 in which R² is as defined above or reacting the compound of Formula 3 with an ammonium salt of the formula NH₄+ −OC(0)R³ in which R³ is hydrogen, (C₁₋₄)alkyl or trifluoro(C₁₋₄)alkyl to give a compound of Formula 2 in which R² is hydrogen, (C₁₋₄)alkyl or trifluoro(C₁₋₄)alkyl, respectively; and (C) optionally separating a mixture of stereoisomers of a compound of Formula 2 to give a single stereoisomer.

13. The process of claim 12 in which n is 1, t is 2, R¹ is fluoro at the 5- and 7-position.

14. The process of claim 13 in which the compound of Formula 3 is reacted with acetamide or ammonium acetate to give a compound of Formula I wherein R² is methyl.

15. The process of claim 13 in which the compound of Formula 3 is reacted with urea to give a compound of Formula I wherein R² is amino.

16. A process for the preparation of a compound of Formula 2:

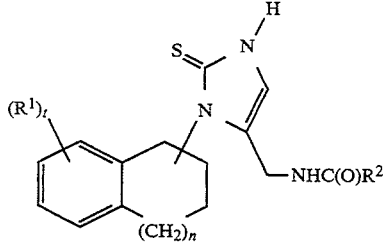

in which:

n is 0, 1 or 2;

t is 0, 1, 2 or 3;

$R^1$ is independently halo, hydroxy or $(C_{1-4})$alkyloxy; and $R^2$ is hydrogen, amino, $(C_{1-4})$alkyl or trifluoro$(C_{1-4})$alkyl; or the individual stereoisomers, or a mixture of stereoisomers thereof; which process comprises:

(A) reacting a compound of Formula 3:

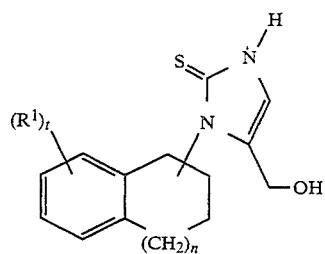

in which n, t and $R^1$ are as defined above, with a primary amide of the formula $H_2NC(O)R^2$ in which $R^2$ is as defined above to give a compound of Formula 2 in which $R^2$ is as defined above or reacting the compound of Formula 3 with an ammonium salt of the formula $NH_4{+} \ {-}OC(O)R^2$ in which $R^2$ is hydrogen, $(C_{1-4})$alkyl or trifluoro$(C_{1-4})$alkyl to give a compound of Formula 2 in which $R^2$ is hydrogen, $(C_{1-4})$alkyl or trifluoro$(C_{1-4})$alkyl, respectively; and (B) optionally separating a mixture of stereoisomers of a compound of Formula 2 to give a single stereoisomer.

17. The process of claim 16 in which n is 1, t is 2, $R^1$ is fluoro at the 5- and 7-position.

18. The process of claim 17 in which the compound of Formula 3 is reacted with acetamide or ammonium acetate to give a compound of Formula I wherein $R^2$ is methyl.

19. The process of claim 18 in which the compound of Formula 3 is reacted with urea to give a compound of Formula I wherein $R^2$ is amino.

* * * * *